(12) United States Patent
Higgins et al.

(10) Patent No.: US 11,076,974 B2
(45) Date of Patent: Aug. 3, 2021

(54) ORTHOTIC ANKLE GARMENT, AND METHOD FOR STABILIZING THE LOWER LEG OF A WEARER

(71) Applicant: ING Source, Inc., Hickory, NC (US)

(72) Inventors: David B. Higgins, Newton, NC (US); Pamela Pearl Haig, Kelley's Island, OH (US); Joe Haig, Kelley's Island, OH (US)

(73) Assignee: ING Source, Inc., Hickory, NC (US)

(\*) Notice: Subject to any disclaimer, the term of this patent is extended or adjusted under 35 U.S.C. 154(b) by 431 days.

(21) Appl. No.: 16/090,470

(22) PCT Filed: Apr. 3, 2017

(86) PCT No.: PCT/US2017/025729
§ 371 (c)(1),
(2) Date: Oct. 1, 2018

(87) PCT Pub. No.: WO2017/173441
PCT Pub. Date: Oct. 5, 2017

(65) Prior Publication Data
US 2019/0110916 A1    Apr. 18, 2019

Related U.S. Application Data

(60) Provisional application No. 62/317,143, filed on Apr. 1, 2016.

(51) Int. Cl.
*A61F 13/00* (2006.01)
*A61F 5/01* (2006.01)
(Continued)

(52) U.S. Cl.
CPC ............ *A61F 5/0111* (2013.01); *A61F 13/06* (2013.01); *A61F 13/08* (2013.01)

(58) Field of Classification Search
CPC ...... A61F 13/06; A61F 13/064; A61F 13/066; A61F 13/067; A61F 5/0111; A61F 5/00;
(Continued)

(56) References Cited

U.S. PATENT DOCUMENTS 4,729,370 A * 3/1988 Kallassy ............... A61F 13/066
602/65
4,844,058 A * 7/1989 Vogelbach ............ A61F 13/066
602/27
(Continued)

FOREIGN PATENT DOCUMENTS

KR    200478268 Y1 * 9/2015 ............. A41B 11/10

*Primary Examiner* — Kim M Lewis
(74) *Attorney, Agent, or Firm* — Schwartz Law Firm, P.C.

(57) ABSTRACT

An orthotic ankle garment is integrally knit of a body yarn, and comprises at least one compression zone incorporating elastic yarns integrated with the body yarn. A lateral fabric brace strap is integrally formed with the body yarn within the compression zone, and is adapted to extend vertically on an outside of the lower leg between the open leg end of the garment and a termination point proximate a lateral malleolus of the ankle. A medial fabric brace strap is integrally formed with the body yarn within the compression zone, and is adapted to extend vertically on an inside of the lower leg between the open leg end of the garment and a termination point proximate a medial malleolus of the ankle. The lateral and medial brace straps define vertically-disposed areas of reduced fabric stretch relative to directly adjacent areas of the compression zone.

16 Claims, 6 Drawing Sheets

(51) Int. Cl.
 *A61F 13/06* (2006.01)
 *A61F 13/08* (2006.01)

(58) Field of Classification Search
 CPC ........ A61F 5/01; A61F 5/0104; A61F 5/0102;
  A61F 5/0585; A61F 5/0127; A61F
  13/0253; A61F 13/00; A61F 13/0246;
  A61F 13/05; A61F 13/053; A61F 13/065;
  A61F 13/068; A61F 13/069; A61F 13/08;
  A61F 13/085; A61H 1/006; A61H 1/00;
  A61H 1/0237; A61H 1/0266; A61H
  2205/12; A61H 2205/125; A61H
  2201/164; A61H 2201/165; A61H
  2203/0406; A41D 13/00; A41D 13/05;
  A41D 13/0543; A41B 11/08; A41B
  11/008; A41B 11/121; A41B 11/123;
  A41B 11/125; A41B 11/126
 See application file for complete search history.

(56) References Cited

U.S. PATENT DOCUMENTS

| | | | |
|---|---|---|---|
| 9,204,986 B2 * | 12/2015 | Higgins | A41D 13/05 |
| 10,799,414 B1 * | 10/2020 | Higgins | A61H 1/00 |
| 2003/0230121 A1 * | 12/2003 | Yokoyama | A41B 11/003 |
| | | | 66/178 A |
| 2006/0085894 A1 * | 4/2006 | Yakopson | A61F 13/08 |
| | | | 2/239 |
| 2006/0247566 A1 * | 11/2006 | Gobet | A61F 13/08 |
| | | | 602/62 |
| 2009/0112140 A1 * | 4/2009 | Gaylord | A61F 5/0102 |
| | | | 602/27 |
| 2009/0165190 A1 * | 7/2009 | Araki | D04B 1/02 |
| | | | 2/240 |
| 2012/0102625 A1 * | 5/2012 | Klein | D04B 1/04 |
| | | | 2/239 |
| 2012/0238929 A1 * | 9/2012 | Grunden | A61F 5/0111 |
| | | | 602/27 |
| 2012/0283611 A1 * | 11/2012 | Matsuo | A41D 13/06 |
| | | | 602/27 |
| 2012/0284902 A1 * | 11/2012 | Matsuo | D04B 1/104 |
| | | | 2/239 |
| 2013/0263629 A1 * | 10/2013 | Gaither | A41B 11/003 |
| | | | 66/185 |
| 2014/0058311 A1 * | 2/2014 | Higgins | A61F 13/064 |
| | | | 602/63 |
| 2016/0076175 A1 * | 3/2016 | Rock | A61F 13/08 |
| | | | 66/171 |
| 2017/0073861 A1 * | 3/2017 | Herold-Herrmann | D04B 1/104 |
| 2017/0172808 A1 * | 6/2017 | Slaski | D04B 1/106 |

\* cited by examiner

ORTHOTIC ANKLE GARMENT, AND METHOD FOR STABILIZING THE LOWER LEG OF A WEARER

TECHNICAL FIELD AND BACKGROUND OF THE DISCLOSURE

The present disclosure relates broadly and generally to compression supports for the lower leg, such as those used for general medical and athletic purposes. In one exemplary embodiment, the invention comprises an orthotic ankle garment, and method for stabilizing the ankle and mid-tarsal joint of a wearer.

The invention comprises an easy-on fit, continuous and stable support. The invention can be comfortably worn under shoes (and under or over socks) or under an ankle foot orthosis or similar product while walking, resting or exercising for added protection, injury prevention and relief of symptoms or conditions associated with numerous pathologies. In exemplary embodiments, the invention supports, stabilizes and reduces unwanted motion of the ankle while boosting circulation. The invention can be used to treat injuries such as Achilles Tendonitis, swollen ankles, painful ankles, and more. It can also stabilize weak ankles, improve balance, and help prevent falls.

SUMMARY OF EXEMPLARY EMBODIMENTS

Various exemplary embodiments of the present disclosure are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

It is also noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that may or may not be utilized in a particular embodiment of the present invention.

According to one exemplary embodiment, the present disclosure comprises an orthotic ankle garment or "sleeve" integrally knit of a body yarn (e.g., in circumferential courses and axial wales), and is adapted for wear on the lower leg of a user; more particularly, over the ankle and foot. The foot of the user comprises the calcaneus, lateral and medial malleolus, talus, midfoot, mid-tarsal joint, metatarso-phalangeal joints, and other bone structure. The portions of the foot and foot anatomy are listed herein to provide antecedent basis for certain functional language recited in the claims and specification below. This listing is not intended to limit application of the exemplary ankle garment only to these portions of the lower leg, as parts of the ankle garment in other embodiments may extend around or over other portions of the ankle, foot and leg.

The term "ankle garment" refers broadly herein to any hosiery or other fabric construction designed to cover at least a portion of the wear's foot. The ankle garment may be knit in whole or in part (e.g., using conventional circular knitting machinery), and may be specially designed for a variety of uses including running, cycling, hiking, golf, hunting, and other general athletic and every-day wear. The present ankle garment may comprise (or be integrally formed with) an open-toe sleeve, foot or ankle wrap, foot sock, tube sock, calf-high sock, mid-calf or over-the calf sock, crew sock, stocking, stretch or support hosiery, or the like.

The term "directly adjacent" in the context of the present disclosure means a fabric area (or "zone") located or formed beside or surrounded, in whole or in part, by another fabric area (or "zone") without intervening fabric, parts or other structure.

The term "axial" or "axial direction" refers herein to mean extending along a generally linear notional axis passing through circumferential portions (e.g., courses) of the garment. For example, the respective compression zones of the exemplary ankle garment may be axially divided- or divided along a generally vertical length such as from the heel upwardly towards the ankle or lower leg, and/or a generally horizontal length such as from the heel towards the toe.

The term "substantially equal" in the context of the present disclosure means within +/−10 percent.

According to one exemplary embodiment, the exemplary orthotic ankle garment is integrally knit of a body yarn, and has an open leg end and an open (or closed) toe end. The ankle garment comprises at least one compression zone incorporating elastic yarns integrated with the body yarn, and extending axially between the open leg and toe ends of the garment. The compression zone is adapted for applying substantially circumferential graduated compression to the lower leg of the user. A lateral fabric brace strap may be separately or integrally formed (e.g., by knitting or weaving) with the body yarn within the compression zone, and is adapted to extend vertically on an outside of the lower leg between the open leg end of the garment and a termination point proximate a lateral malleolus of the ankle. The lateral brace strap defines a vertically-disposed area of reduced fabric stretch relative to directly adjacent areas of the compression zone. A medial fabric brace strap may be separately or integrally formed (e.g., by knitting or weaving) with the body yarn within the compression zone, and is adapted to extend vertically on an inside of the lower leg between the open leg end of the garment and a termination point proximate a medial malleolus of the ankle. The medial brace strap defines a vertically-disposed area of reduced fabric stretch relative to directly adjacent areas of the compression zone. In alternative exemplary embodiments, the ankle garment may incorporate only one of the medial and lateral brace straps.

According to another exemplary embodiment, an upwardly-turned lateral stabilizer wing is located adjacent the termination point of the lateral brace strap, and is configured to extend proximate the lateral malleolus of the ankle upward towards a top region of the foot. The lateral stabilizer wing defines an area of reduced fabric stretch relative to directly adjacent areas of the compression zone.

According to another exemplary embodiment, an upwardly-turned medial stabilizer wing is located adjacent the termination point of the medial brace strap, and is configured to extend proximate the medial malleolus of the ankle upward towards a top region of the foot. The medial stabilizer wing defines an area of reduced fabric stretch relative to directly adjacent areas of said compression zone.

According to another exemplary embodiment, a midfoot stabilizer bar is located at a base of the lateral stabilizer wing, and is configured to extend axially adjacent a lateral midfoot region of the foot. The midfoot stabilizer bar defines an area of reduced fabric stretch relative to directly adjacent areas of the compression zone.

According to another exemplary embodiment, a skin-adhesive gel is applied to an inside of the garment in the area defined by the midfoot stabilizer bar.

According to another exemplary embodiment, the at least one compression zone comprises a first high compression zone axially spaced apart from the toe end of the ankle garment and adapted for applying at least 20 mmHg of substantially circumferential compression around a midfoot region of the foot. Within the first high compression zone, the elastic yarns are adapted for applying course-to-course graduated compression to the foot of the user increasing in an axial direction within the zone towards the toe end of the garment. Graduated compression may be achieved by laying-in elastic yarns of strategic lengths or denier (thickness). From the first high compression zone, the exemplary ankle garment comprises reduced compression axially towards the toe end of the garment.

According to another exemplary embodiment, the at least one compression zone further comprises a second high compression zone axially spaced apart from the leg end of the ankle garment and adapted for applying at least 20 mmHg of substantially circumferential compression around the ankle of the user. Within the second high compression zone, the elastic yarns are adapted for applying course-to-course graduated compression to the foot of the user increasing in an axial direction within the zone towards the open leg end of the garment. Graduated compression may be achieved by laying-in elastic yarns of strategic lengths or denier (thickness). From the second high compression zone, the exemplary ankle garment comprises reduced compression axially towards the leg end of the garment.

According to another exemplary embodiment, the at least one compression zone further comprises a pressure relief zone formed at an anatomical turn of the ankle garment, and shaped to closely fit a heel and upper instep region of the foot. The pressure relief zone extends around the foot between said first and second high compression zones for separating said first and second high compression zones, and configured to apply less circumferential compression to the foot as compared to the compression applied by said first and second high compression zones. In one embodiment, the pressure relief zone incorporates a thinner fabric substantially devoid of elastic yarns thereby applying reduced compression to the foot in an area between the first and second high compression zones. The exemplary pressure relief zone is configured to extend over a top of the foot proximate an ankle joint of the user, and further comprises a reduced compression heel pocket formed between the first and second high compression zones.

According to another exemplary embodiment, the at least one compression zone further comprises a first moderate compression zone adjacent the first high compression zone and extending axially towards the toe end of the garment. The first moderate compression zone comprises elastic yarns integrated with the body yarn, and adapted for applying course-to-course graduated compression to the foot of the user increasing in an axial direction towards the toe end of the garment. Graduated compression may be achieved by laying-in elastic yarns of strategic lengths or denier (thickness). The first moderate compression zone is adapted for applying less circumferential compression to the foot as compared to the compression applied by the first high compression zone. In one embodiment, the first moderate compression zone applies between 10%-50% less compression to the foot as compared to the compression applied by the first high compression zone.

According to another exemplary embodiment, the at least one compression zone further comprises a first light compression zone residing adjacent the first moderate compression zone at the toe end of the ankle garment. The first light compression zone is adapted for applying less circumferential compression to the foot as compared to the compression applied by the first moderate compression zone. In one embodiment, the first light compression zones applies between 10%-50% less compression to the foot as compared to the compression applied by the first moderate compression zone.

According to another exemplary embodiment, the at least one compression zone further comprises a second moderate compression zone extending axially between the leg end of the ankle garment and the second high compression zone. The second moderate compression zone comprises elastic yarns integrated with the body yarn, and adapted for applying course-to-course graduated compression to the foot of the user decreasing in an axial direction towards the open leg end of the garment. Graduated compression may be achieved by laying-in elastic yarns of strategic lengths or denier (thickness). The second moderate compression zone is adapted for applying less circumferential compression to the lower leg as compared to the compression applied by the second high compression zone. In one embodiment, the second moderate compression zone applies between 10%-50% less compression to the foot as compared to the compression applied by the second high compression zone.

According to another exemplary embodiment, the at least one compression zone further comprises a second light compression zone residing adjacent the second moderate compression zone at the leg end of the ankle garment. The second light compression zone is adapted for applying less circumferential compression to the lower leg as compared to the compression applied by the second moderate compression zone. In one embodiment, the second light compression zones applies between 10%-50% less compression to the foot as compared to the compression applied by the second moderate compression zone.

According to another exemplary embodiment, the first light compression zone at the toe end of the garment comprises a flat-knit toe welt (or toe closure).

According to another exemplary embodiment, the second light compression zone at the leg end of said garment comprises a folded ankle welt.

In yet another exemplary embodiment, the disclosure comprises a method for bracing a lower leg of a user (the lower leg including an ankle and foot). The method comprises applying an orthotic ankle garment to the lower leg. The ankle garment has at least one compression zone adapted for applying substantially circumferential compression to the ankle and foot. Lateral and medial brace straps are integrally formed within the garment within the compression zone. The orthotic ankle garment is worn such that the lateral brace strap extends vertically on an outside of the lower leg between an open leg end of the garment and a termination point proximate a lateral malleolus of the ankle. The lateral brace strap defines a vertically-disposed area of reduced fabric stretch relative to directly adjacent areas of the compression zone. The medial brace strap extends vertically on an inside of the lower leg between the open leg end of the garment and a termination point proximate a medial malleolus of the ankle. The medial brace strap defines a vertically-disposed area of reduced fabric stretch relative to directly adjacent areas of the compression zone.

BRIEF DESCRIPTION OF THE DRAWINGS

Exemplary embodiments of the present invention will hereinafter be described in conjunction with the following drawing figures, wherein like numerals denote like elements, and wherein.

DESCRIPTION OF EXEMPLARY EMBODIMENTS AND BEST MODE

The present invention is described more fully hereinafter with reference to the accompanying drawings, in which one or more exemplary embodiments of the invention are shown. Like numbers used herein refer to like elements throughout. This invention may, however, be embodied in many different forms and should not be construed as limited to the embodiments set forth herein; rather, these embodiments are provided so that this disclosure will be operative, enabling, and complete. Accordingly, the particular arrangements disclosed are meant to be illustrative only and not limiting as to the scope of the invention, which is to be given the full breadth of the appended claims and any and all equivalents thereof. Moreover, many embodiments, such as adaptations, variations, modifications, and equivalent arrangements, will be implicitly disclosed by the embodiments described herein and fall within the scope of the present invention.

Although specific terms are employed herein, they are used in a generic and descriptive sense only and not for purposes of limitation. Unless otherwise expressly defined herein, such terms are intended to be given their broad ordinary and customary meaning not inconsistent with that applicable in the relevant industry and without restriction to any specific embodiment hereinafter described. As used herein, the article "a" is intended to include one or more items. Where only one item is intended, the term "one", "single", or similar language is used. When used herein to join a list of items, the term "or" denotes at least one of the items, but does not exclude a plurality of items of the list.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Figure 1:
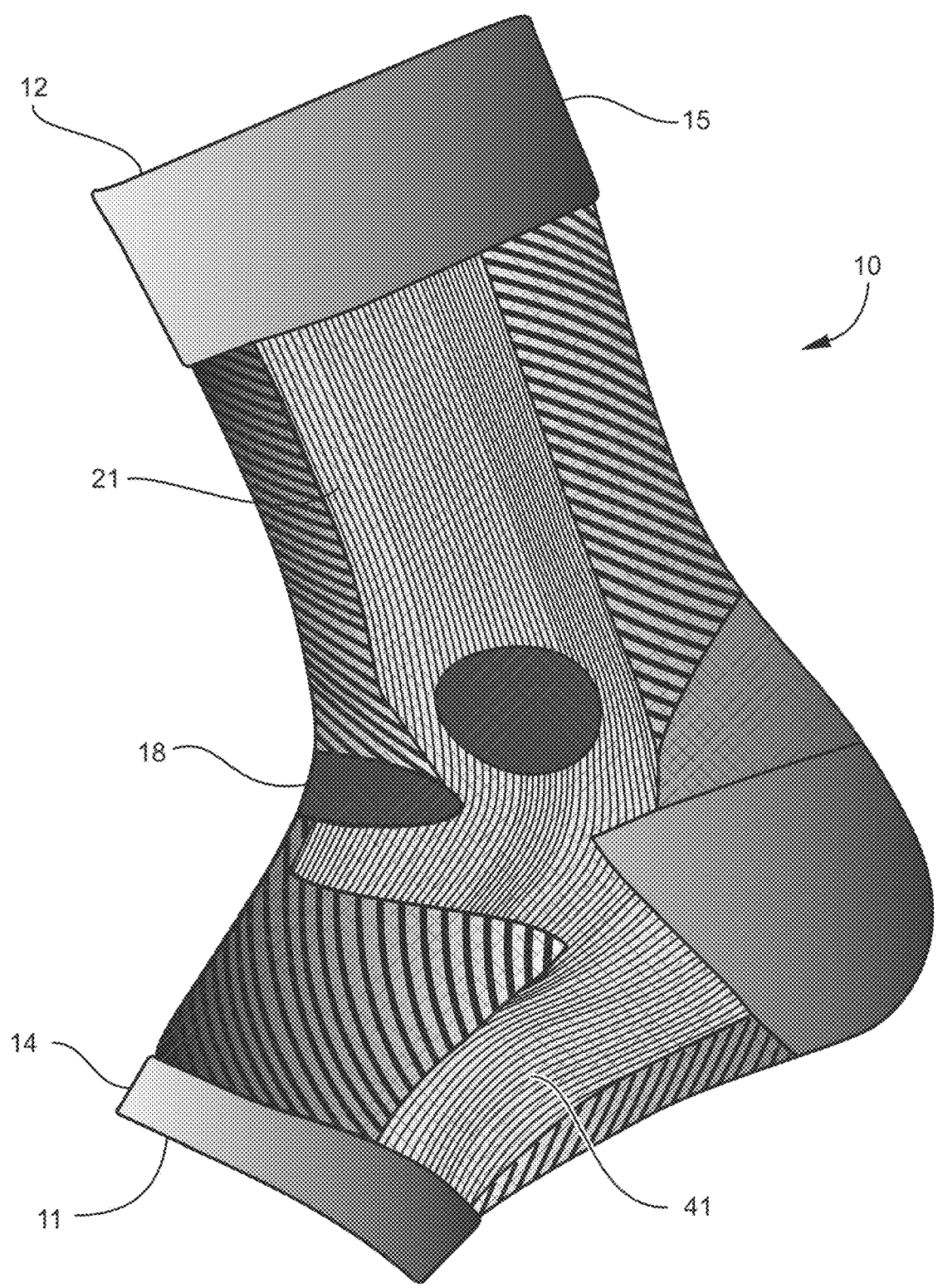
FIG. 1 is a view of the exemplary orthotic ankle garment showing various features and elements located on a lateral side (outer side) of the garment.

Referring now specifically to the drawings, a one-piece orthotic ankle garment according to one exemplary embodiment of the present disclosure is illustrated in FIG. 1, and shown generally at broad reference numeral 10. The exemplary ankle garment 10 may be formed throughout of a closed-loop Jersey-knit body yarn comprising micro-nylon, moisture wicking fibers, and/or other natural or synthetic fibers or fiber blends. Elastic yarns, such as a spandex or other elastomer, are laid-in the body yarn in predetermined areas of the ankle garment 10 to create multiple distinct zones of graduated circumferential compression. One exemplary construction comprises approximately 76% 140-denier micro-nylon and 24% 280-denier LYCRA® (spandex). In the exemplary embodiment, the present ankle garment may be constructed on a circular hosiery knitting machine integrating a plurality of yarns formed in needle and sinker loops extending in circumferential courses and axial wales.

One commercial example of a circular knitting machine capable of producing the present ankle garment may be the "CC4-MED" machine manufactured by Merz Maschinenfabrik GmbH of Hechingen, Germany. The CC4-MED comprises a 4-feed, high-efficiency, single-cylinder circular knitting machine for the production of various compression garments in compression classes I to III. The Merz positive feeders enable the feeding-in of inlay yarns to produce the desired compression with controlled feed-in yarn tension in each mesh course. Alternatively, the exemplary ankle garment may be fabricated according to other known techniques, such as by cut-and-sew of elasticized fabric from pre-designed patterns, with flat lock stitching.

Figure 2:
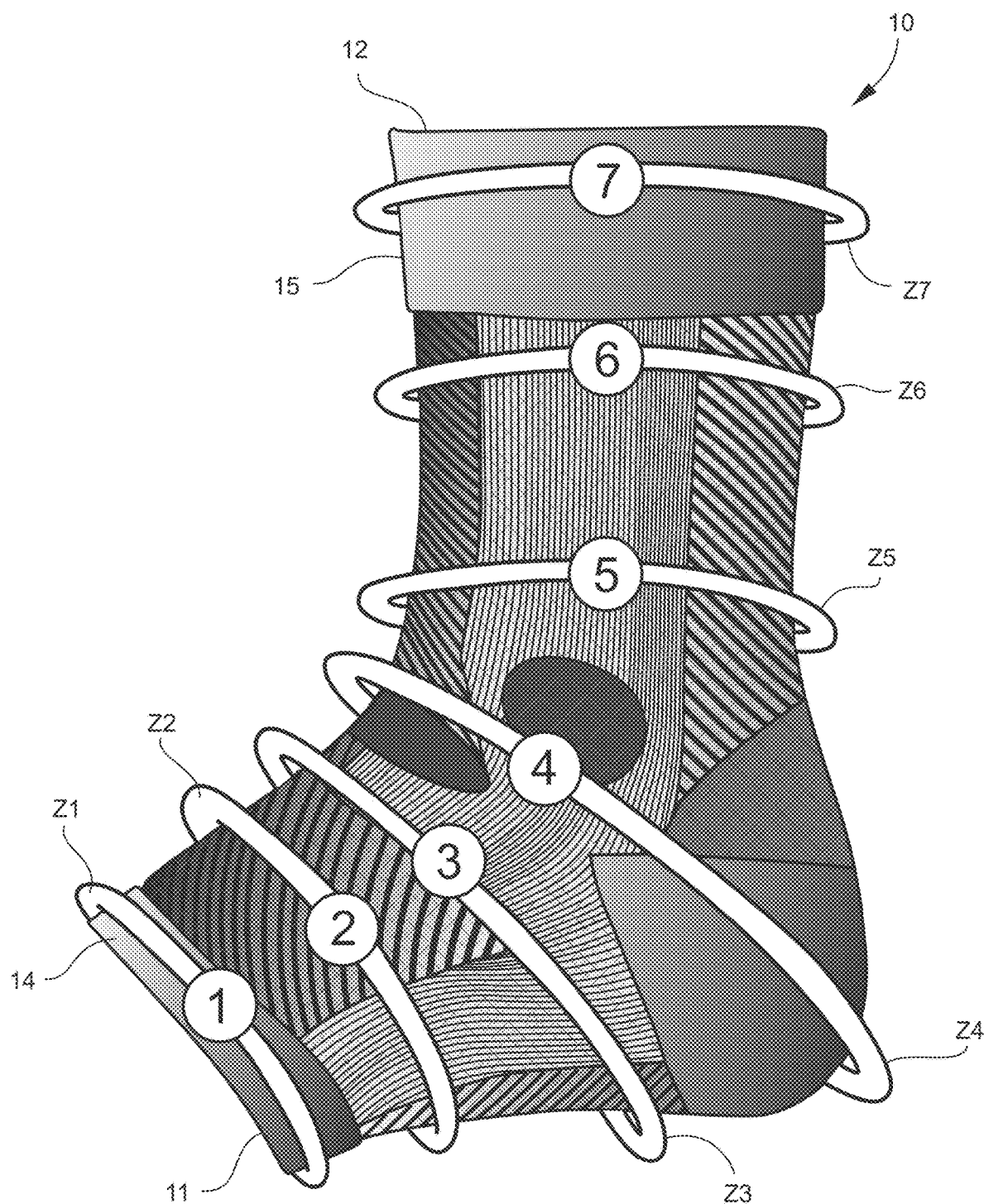
FIG. 2 is a view of the exemplary orthotic ankle garment indicating generally the various zones of circumferential compression.

The exemplary ankle garment 10 is divided into axially adjacent circumferential regions, identified in FIG. 2 as zones Z1-Z7. These circumferential regions define respective therapeutic zones of designated compression designed to closely and comfortably fit the garment 10 to the user, while strategically supporting the ankle and foot. The circumferential zones Z1-Z7 of the exemplary ankle garment 10 are located to apply predetermined degrees of compression to various parts of the lower leg. Targeted compression in zones Z1-Z7 may be graduated by laying-in or "integrating" elastic yarns of strategic lengths or denier (thickness) with the body yarn of the garment 10 in the different axially-divided garment regions. In one exemplary embodiment, garment regions Z1 and Z7 comprise zones of relatively light compression, garment regions Z2 and Z6 comprise zones of relatively moderate compression, garment region Z4 comprises a "pressure relief" zone of relatively moderate compression, and garment regions Z3 and Z5 comprise zones of relatively high compression.

The knit construction in light compression zones Z1 and Z7 includes elastic yarns laid-in body yarns of the ankle garment 10, and increasing in length in a course-to-course axial direction towards to the open toe end 11 and leg end 12 of the garment 10. Exemplary zone Z1 defines a non-binding flex band or "welt" 14, and is knitted from 0.5-1.0 inch in relaxed axial width from the toe end 11 of the garment 10. Zone Z1 may comprise between 20-30 courses of body yarn, and may be configured to apply compression to the foot in the range of 10-15 mmHg, or less. Exemplary zone Z7 comprises a relatively wide, smooth and comfortable fabric band 15 with a relaxed axial width ranging from 1-3 inches from the open leg end 12 of the garment 10. This wide band 15 is designed to hold the garment 10 in place during wear, and may incorporate skin-adhering gels or other texture on its inside surface. The compression applied to the foot in zone Z7 may also be in the range of 10-15 mmHg, or less. The light compression zones Z1 and Z7 are designed to apply between 10%-50% less compression to the foot and ankle of the wearer as compared to the compression applied by the moderate compression zones Z2 and Z6.

The moderate compression zones Z2 and Z6 reside directly axially adjacent the light compression zones Z1 and Z2, respectively, and comprise elastic yarns laid-in the body yarn of the garment 10. The elastic yarns are strategically formed to provide increased graduated compression in a course-to-course axial direction from respective light compression zones Z1 and Z7 towards the high compression zones Z3 and Z5. In the exemplary ankle garment 10, each moderate compression zone Z2, Z6 may comprise between 40-60 courses of body yarn. The moderate compression zones Z2 and Z6 are knitted from 1-2 inches in relaxed axial width, and may be designed to apply graduated circumferential compression in the range of 15-20 mmHg. According to one exemplary embodiment, the moderate compression zone applies between 10%-50% less compression to the foot and ankle of the wearer as compared to the compression applied by the high compression zones Z3 and Z5.

The high or "firm" compression zones Z3 and Z5 reside directly axially adjacent the moderate compression zones Z2 and Z6, respectively, and comprise elastic yarns laid-in the body yarn in successive courses of the garment. The high compression zones Z3 and Z5 may be knitted from 1-2 inches in relaxed axial width, and may be designed to apply graduated compression to the foot and ankle in the range of 20-30 mmHg. Each zone Z3 and Z5 may comprise between 40-60 courses of body yarn.

The pressure relief zone Z4 is formed between and directly axially adjacent the high compression zones Z3 and Z5 at the anatomical turn of the garment 10, and is shaped to closely fit the heel and upper instep of the foot. The garment heel in this region has a deep-formed pocket, made via reciprocation (knitting on one side). The upper instep has an oval shaped area 18 of thinner fabric which may be substantially devoid of elastic yarns to minimize bunching and thickness at the turn of the foot and ankle. Compression in this pressure relief zone Z4 may be less than 15 mmHg.

Figure 3:
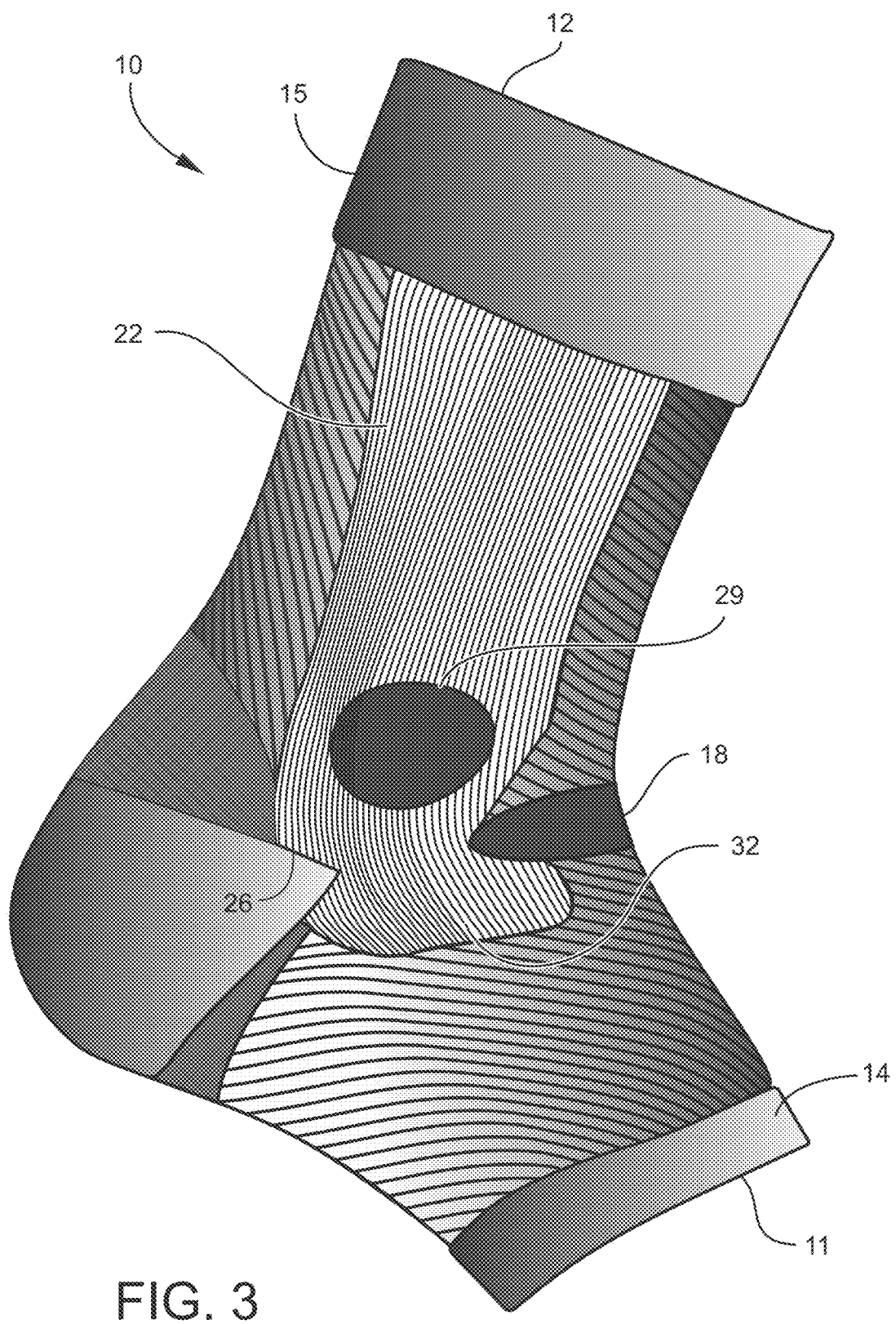
FIG. 3 is a further view of the exemplary orthotic ankle garment showing various features and elements located on a medial side (inner side) of the garment.
Figure 4:
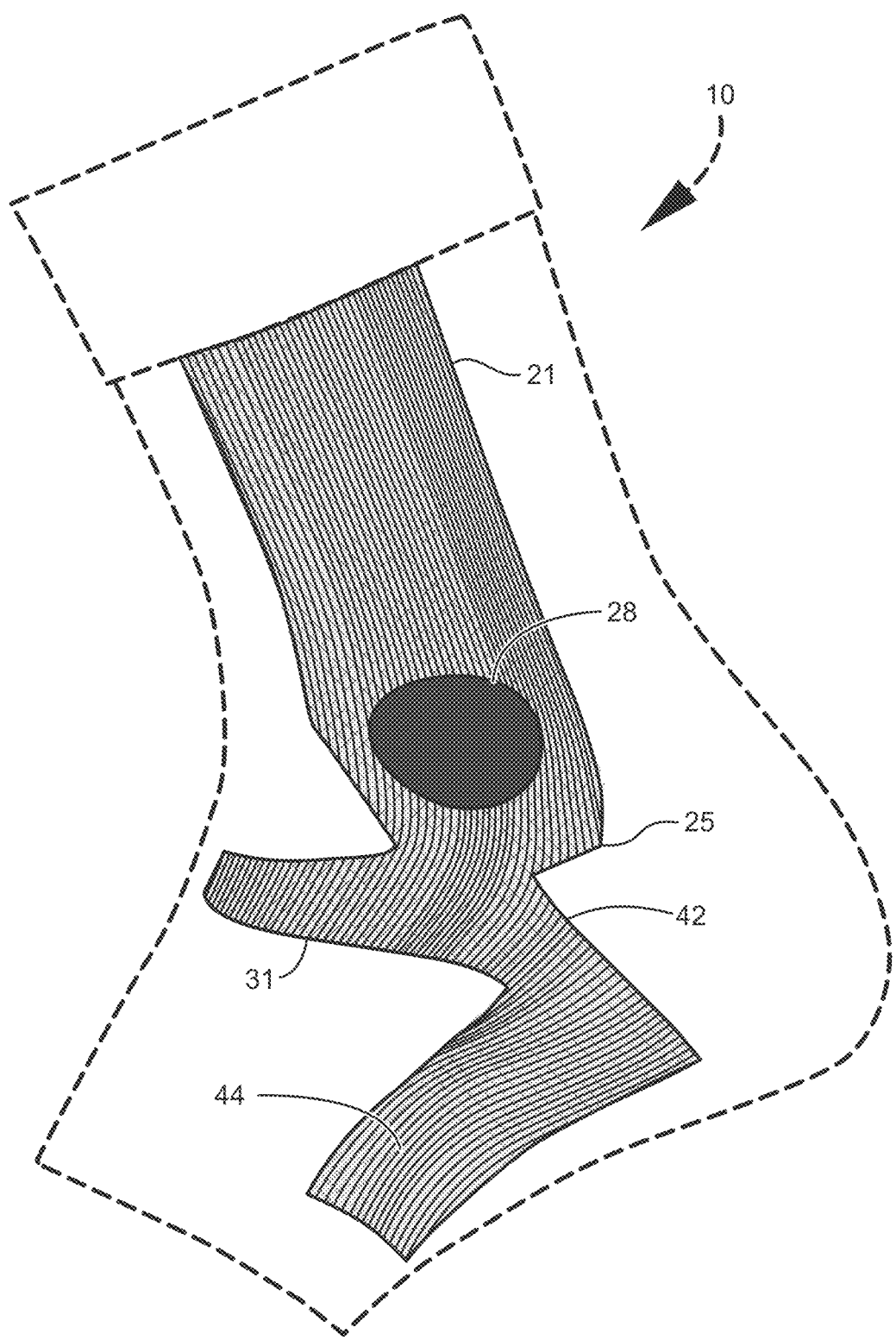
FIG. 4 shows various areas of increased lateral stabilization formed with the ankle garment.

Referring to FIGS. 1, 3, and 4, the exemplary ankle garment 10 further comprises lateral and medial fabric brace straps 21, 22 integrally formed (e.g., by knitting or weaving) with the body yarn of the garment 10, and configured to extend vertically on the outside and inside of the lower leg of the wearer. The lateral brace strap 21 extends between the open leg end 12 of the garment 10 and a termination point 25 located to reside proximate a lateral malleolus of the ankle. The medial brace strap 22 extends between the open leg end 12 of the garment 10 and a termination point 26 located to reside proximate a medial malleolus of the ankle. Each brace strap 21, 22 extends vertically substantially through circumferential compression zones Z4, Z5, and Z6 described above, and defines an area of reduced fabric stretch relative to directly adjacent fabric structure of the garment 10.

In one exemplary embodiment, the low-stretch lateral and medial brace straps 21, 22 are integrated into the garment 10 using a "locked down" knitting technique feeding multiple ends through a single feed. The resulting increased body yarn and flattened loops define fabric areas of up to 50% reduced stretch in both the course-wise and wale-wise directions, as compared to the immediately surrounding fabric structure in zones Z4, Z5, and Z6 of the garment 10. The low-stretch brace straps 21, 22 function in a manner similar to low stretch athletic tape, such as that used for therapeutic taping to create motion control in injured limbs or to prevent injury in performing athletes or ambulatory patients. The low-stretch brace straps 21, 22 are configured to run vertically on the lateral and medial sides of the ankle beginning approximately 3 inches above the lateral and medial malleolus (ankle bone), respectively. Each brace strap 21, 22 may incorporate a small circular area 28, 29 of thinner fabric with greater stretch to minimize excess pressure on the protruding malleolus.

As best shown in FIGS. 1 and 4, an upwardly-turned lateral stabilizer wing 31 is located adjacent the termination point 25 of the lateral brace strap 21, and is configured to extend proximate the lateral malleolus of the ankle and curve upward towards a top region of the foot. In one embodiment, the lateral stabilizer wing 31 has a length of approximately 1-2 inches, and resides substantially within compression zone Z3 of the garment 10. The lateral stabilizer wing 31 may be fabricated according to the same locked-down knitting technique used to integrate the brace straps 21, 22 in the garment, and may define a fabric area of up to 50% reduced stretch in both the course-wise and wale-wise directions as compared to the immediately surrounding fabric structure of the garment 10.

Figure 6:
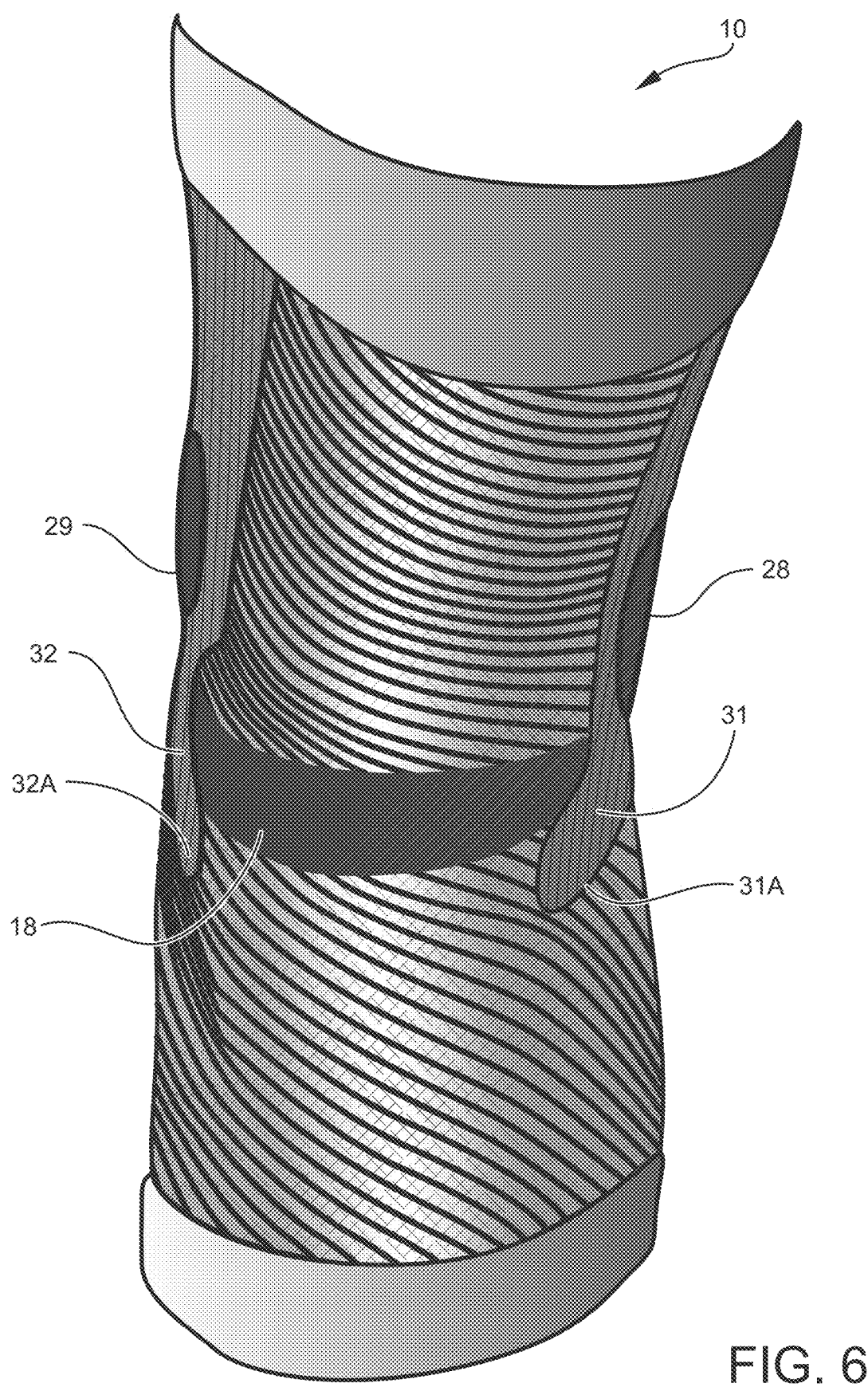
FIG. 6 is a front perspective view of the exemplary ankle garment.

As shown in FIG. 3, an upwardly-turned medial stabilizer wing 32 is located adjacent the termination point 26 of the medial brace strap 22, and is configured to extend proximate the lateral malleolus of the ankle and curve upward towards a top region of the foot. In one embodiment, the medial stabilizer wing 32 has a length of approximately 1-2 inches, and resides substantially within compression zone Z3 of the garment 10. The medial stabilizer wing 32 may be fabricated according to the same locked-down knitting technique used to integrate the brace straps 21, 22 in the garment 10, and may define a fabric area of up to 50% reduced stretch in both the course-wise and wale-wise directions as compared to the immediately surrounding fabric structure of the garment 10. Distal ends 31A, 32A of the stabilizer wings 31, 32 converge or point, as shown in FIG. 6, towards the upper midfoot to cover the mid-tarsal joint (tarsal sinus)—offering further support and motion control at the top of the foot.

Figures 5, 5A:
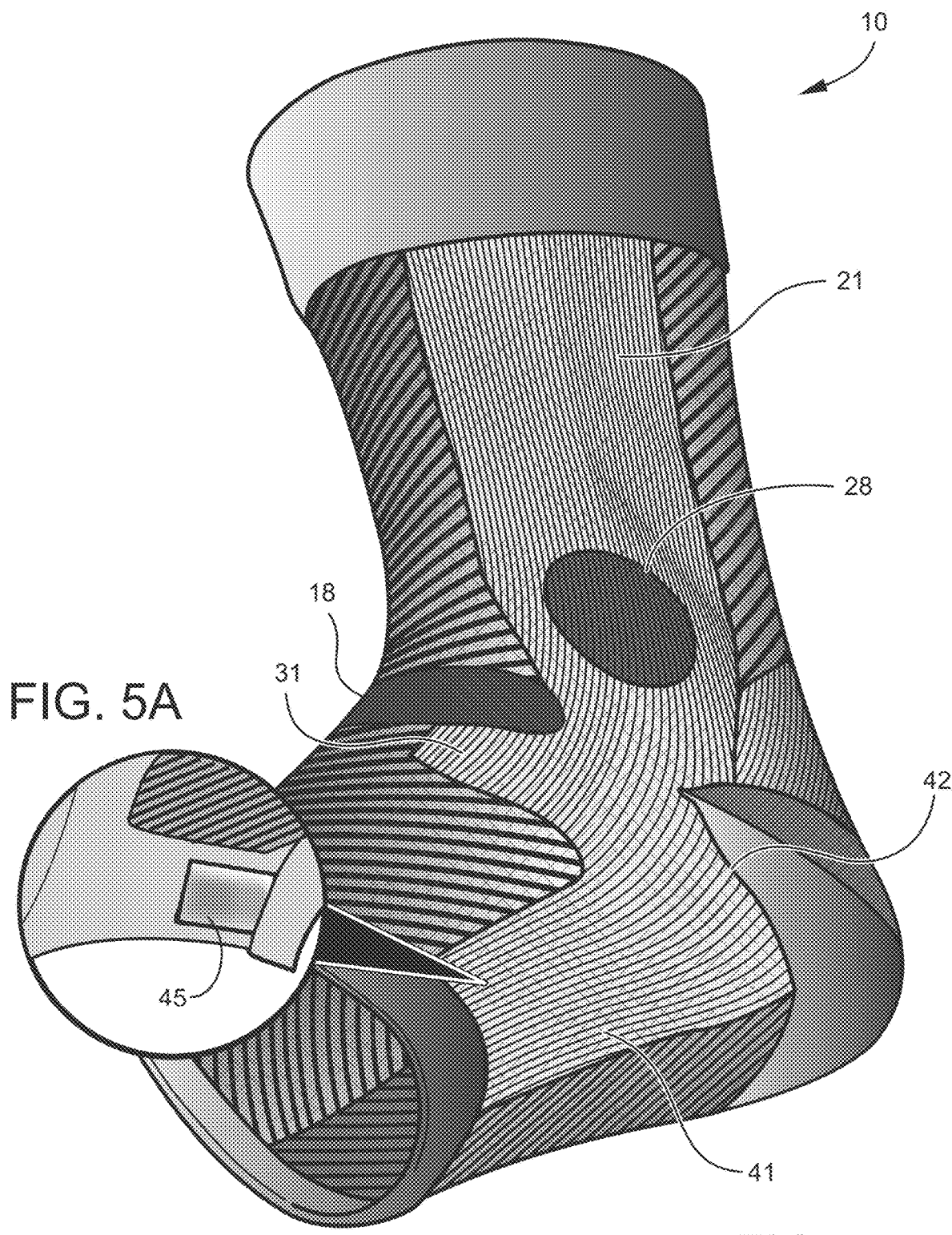
FIG. 5 is a perspective view of the exemplary ankle garment.
FIG. 5A shows the gel stabilizer located on an inside portion of the ankle garment.

Referring to FIG. 5, the exemplary ankle garment 10 may further comprise a midfoot stabilizer bar 41 located at a base of the lateral stabilizer wing 31. The exemplary stabilizer bar 41 is configured to extend axially adjacent a lateral midfoot region of the foot and terminate at approximately the middle of the 5$^{th}$ metatarsal bone. In the exemplary embodiment, the stabilizer bar 41 is integrally formed with the lateral stabilizer wing 31 at a hinge point 42 slightly forward of the heel pocket. The stabilizer bar 41 may also be fabricated according to the same locked-down knitting technique used to integrate the brace straps 21, 22 in the garment 10, and may define a fabric area of up to 50% reduced stretch in both the course-wise and wale-wise directions as compared to the immediately surrounding fabric structure of the garment 10.

Additionally, a skin-adhesive gel 45 (See FIG. 5A) may be applied to an inside of the garment 10 in the area defined by the midfoot stabilizer bar 41—residing adjacent a lateral midfoot region of the foot proximate a base of the 5th metatarsal bone. The exemplary midfoot stabilizer bar 41 and gel 45 cooperate to form a bracing element designed to stabilize the talus and mid-tarsal joints without immobilizing the foot. This promotes lateral stabilization for inversion resistance to neutralize unsafe motion. In one exemplary embodiment, the skin-adhesive gel 45 comprises a low durometer silicone gel or other comparable substance or element capable of adhering to the skin. The exemplary gel 45 may be applied to the garment 10 in a hot liquid form using a screen and pressing bar, such that a thin layer of the material melts, absorbs, and fuses into the fabric. The fabric is then heated to cure the gel 45, thereby permanently integrating and locking it into the garment 10. In one embodiment, the gel 45 covers a portion of the inside rectangular area of the midfoot stabilizer bar 41. When the garment 10 is worn on a bare foot, the gel 45 adheres to the skin in a similar fashion to athletic tape, and creates a pulling force on the foot toward the lateral side for purposes of "locking" or strengthening the mid-tarsal joint.

The low-stretch lateral and medial brace straps 21, 22, stabilizer wings 31, 32, lateral stabilizer bar 41, and gel 45 function in combination to effectively brace the lower leg to the shape and pattern of the ankle garment 10. By applying this combination of construction, an orthopedic structure offering semi-rigid medial and lateral resistance is applied to the user's foot and ankle. The skin-adhering gel 45 applied in this embodiment stabilizes the movement of the foot towards the lateral side, and thereby reduces ankle joint weakness or movement which may cause over inversion or eversion of the ankle and foot. The lateral and medial brace straps 21, 22 function as fabric "stays" to stabilize the lower leg with a flexible rigidity—without the use of rigid plastic or metal bars for stabilizing the ankle.

For the purposes of describing and defining the present invention it is noted that the use of relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

Exemplary embodiments of the present invention are described above. No element, act, or instruction used in this description should be construed as important, necessary, critical, or essential to the invention unless explicitly described as such. Although only a few of the exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under 35 U.S.C. § 112(f) [or 6th paragraph/pre-AIA] is not intended. Additionally, it is not intended that the scope of patent protection afforded the present invention be defined by reading into any claim a limitation found herein that does not explicitly appear in the claim itself.

What is claimed:

1. An orthotic ankle garment integrally knit of a body yarn and adapted for wear on a lower leg of a user, the lower leg including an ankle and foot, said orthotic ankle garment having an open leg end and a toe end, and further comprising:
   at least one compression zone comprising elastic yarns integrated with said body yarn, and extending axially between the open leg and toe ends of said garment, and said compression zone adapted for applying substantially circumferential compression to the lower leg of the user;
   a lateral brace strap integrally formed within said compression zone, and adapted to extend vertically on an outside of the lower leg between the open leg end of said garment and a termination point proximate a lateral malleolus of the ankle, said lateral brace strap defining a vertically-disposed area of reduced fabric stretch relative to directly adjacent areas of said compression zone; and
   a medial brace strap integrally formed within said compression zone, and adapted to extend vertically on an inside of the lower leg between the open leg end of said garment and a termination point proximate a medial malleolus of the ankle, said medial brace strap defining a vertically-disposed area of reduced fabric stretch relative to directly adjacent areas of said compression zone;
   an upwardly-turned lateral stabilizer wing located at the termination point of said lateral brace strap, and configured to extend proximate the lateral malleolus of the ankle towards a top region of the foot, and said lateral stabilizer wing defining an area of reduced fabric stretch relative to directly adjacent areas of said compression zone.

2. The orthotic ankle garment according to claim 1, and comprising an upwardly-turned medial stabilizer wing located at the termination point of said medial brace strap, and configured to extend proximate the medial malleolus of the ankle towards a top region of the foot, and said medial stabilizer wing defining an area of reduced fabric stretch relative to directly adjacent areas of said compression zone.

3. The orthotic ankle garment according to claim 2, and comprising a midfoot stabilizer bar located at a base of said lateral stabilizer wing, and configured to extend axially adjacent a lateral midfoot region of the foot, and said midfoot stabilizer bar defining an area of reduced fabric stretch relative to directly adjacent areas of said compression zone.

4. The orthotic ankle garment according to claim 3, and comprising a skin-adhesive gel applied to an inside portion of said garment in the area defined by said midfoot stabilizer bar.

5. The orthotic ankle garment according to claim 1, wherein said at least one compression zone comprises a first high compression zone axially spaced apart from the toe end of said ankle garment and adapted for applying at least 20 mmHg of substantially circumferential compression around a midfoot region of the foot, and wherein said ankle garment comprises reduced compression axially from said first high compression zone towards the toe end of said garment.

6. The orthotic ankle garment according to claim 5, wherein said at least one compression zone further comprises a second high compression zone axially spaced apart from the leg end of said ankle garment and adapted for applying at least 20 mmHg of substantially circumferential compression around the ankle of the user, and wherein said ankle garment comprises reduced compression axially from said second high compression zone to the leg end of said garment.

7. The orthotic ankle garment according to claim 6, wherein said at least one compression zone further comprises a pressure relief zone formed at an anatomical turn of said ankle garment, and shaped to closely fit a heel and upper instep region of the foot, said pressure relief zone extending around the foot between said first and second high compression zones for separating said first and second high compression zones, and configured to apply less circumferential compression to the foot as compared to the compression applied by said first and second high compression zones.

8. The orthotic ankle garment according to claim 7, wherein said at least one compression zone further comprises a first moderate compression zone adjacent said first high compression zone and extending axially towards the toe end of said garment, said first moderate compression zone adapted for applying less circumferential compression to the foot as compared to the compression applied by said first high compression zone.

9. The orthotic ankle garment according to claim 8, wherein said at least one compression zone further comprises a first light compression zone residing adjacent said first moderate compression zone at the toe end of said ankle garment, said first light compression zone adapted for applying less circumferential compression to the foot as compared to the compression applied by said first moderate compression zone.

10. The orthotic ankle garment according to claim 9, wherein said at least one compression zone further comprises a second moderate compression zone extending axially between the leg end of said ankle garment and said second high compression zone, said second moderate compression zone adapted for applying less circumferential compression to the lower leg as compared to the compression applied by said second high compression zone.

11. The orthotic ankle garment according to claim 10, wherein said at least one compression zone further comprises a second light compression zone residing adjacent said second moderate compression zone at the leg end of said ankle garment, said second light compression zone adapted for applying less circumferential compression to the lower leg as compared to the compression applied by said second moderate compression zone.

12. The orthotic ankle garment according to claim 11, wherein said second light compression zone at the leg end of said garment comprises a folded ankle welt.

13. An orthotic ankle garment integrally knit of a body yarn and adapted for wear on a lower leg of a user, the lower leg including an ankle and foot, said orthotic ankle garment having an open leg end and a toe end, and comprising:
 a first high compression zone axially spaced apart from the toe end of said garment and adapted for applying at least 20 mmHg of substantially circumferential compression around a midfoot region of the foot, and wherein said ankle garment comprises reduced compression axially from said first high compression zone towards the toe end of said garment;
 a second high compression zone axially spaced apart from the leg end of said garment and adapted for applying at least 20 mmHg of substantially circumferential compression around the ankle of the user, and wherein said ankle garment comprises reduced compression axially from said second high compression zone to the leg end of said garment;
 a pressure relief zone formed at an anatomical turn of said ankle garment, and shaped to closely fit a heel and upper instep region of the foot, said pressure relief zone extending around the foot between said first and second high compression zones for separating said first and second high compression zones, and configured to apply less circumferential compression to the foot as compared to the compression applied by said first and second high compression zones;
 a lateral brace strap integrally formed with the body yarn of said garment, and adapted to reside on an outside of the lower leg between the open leg end of said garment and a termination point proximate a lateral malleolus of the ankle, said lateral brace strap extending axially through said second high compression zone, and defining a vertically-disposed area of reduced fabric stretch relative to directly adjacent areas of said second high compression zone; and
 a medial brace strap integrally formed with the body yarn of said garment, and adapted to reside on an inside of the lower leg between the open leg end of said garment and a termination point proximate a medial malleolus of the ankle, said medial brace strap extending axially through said second high compression zone, and defining a vertically-disposed area of reduced fabric stretch relative to directly adjacent areas of said second high compression zone;
 an upwardly-turned lateral stabilizer wing located at the termination point of said lateral brace strap, said lateral stabilizer wing residing within said first high compression zone, and configured to extend proximate the lateral malleolus of the ankle towards a top region of the foot, and said lateral stabilizer wing defining an area of reduced fabric stretch relative to directly adjacent areas of said compression zone.

14. The orthotic ankle garment according to claim 13, and comprising an upwardly-turned medial stabilizer wing located at the termination point of said medial brace strap, said medial stabilizer wing residing within said first high compression zone, and configured to extend proximate the medial malleolus of the ankle towards a top region of the foot, and said medial stabilizer wing defining an area of reduced fabric stretch relative to directly adjacent areas of said compression zone.

15. The orthotic ankle garment according to claim 14, and comprising a midfoot stabilizer bar located at a base of said lateral stabilizer wing, and configured to extend axially adjacent a lateral midfoot region of the foot, and said midfoot stabilizer bar defining an area of reduced fabric stretch relative to directly adjacent areas of said compression zone.

16. The orthotic ankle garment according to claim 15, and comprising a skin-adhesive gel applied to an inside of said garment in a portion of area defined by said midfoot stabilizer bar.

\* \* \* \* \*